United States Patent
Kawajiri

(10) Patent No.: US 12,150,732 B2
(45) Date of Patent: Nov. 26, 2024

(54) APPARATUS FOR UNLOCKING DOOR TO ROOM CONTAINING AN MRI APPARATUS

(71) Applicant: CANON MEDICAL SYSTEMS CORPORATION, Otawara (JP)

(72) Inventor: Sho Kawajiri, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 584 days.

(21) Appl. No.: 17/342,891

(22) Filed: Jun. 9, 2021

(65) Prior Publication Data
US 2021/0393131 A1    Dec. 23, 2021

(30) Foreign Application Priority Data
Jun. 22, 2020  (JP) .................. 2020-107219

(51) Int. Cl.
| | | |
|---|---|---|
| G07C 9/22 | (2020.01) | |
| A61B 5/00 | (2006.01) | |
| A61B 5/055 | (2006.01) | |
| G01R 33/28 | (2006.01) | |
| G01R 33/54 | (2006.01) | |
| G07C 9/00 | (2020.01) | |
| G07C 9/27 | (2020.01) | |
| G07C 9/28 | (2020.01) | |

(52) U.S. Cl.
CPC ............ *A61B 5/0046* (2013.01); *A61B 5/055* (2013.01); *A61B 5/74* (2013.01); *G07C 9/00571* (2013.01); *G07C 9/22* (2020.01); *G07C 9/27* (2020.01); *G07C 9/28* (2020.01); *G01R 33/288* (2013.01); *G01R 33/546* (2013.01)

(58) Field of Classification Search
CPC .. G01R 33/288; G01R 33/546; G01R 33/543; G01R 33/20; A61B 5/0046; A61B 5/055; A61B 5/74; G07C 9/22; G07C 9/27; G07C 9/28; G07C 9/00571; G07C 9/00563
See application file for complete search history.

(56) References Cited

U.S. PATENT DOCUMENTS

| | | | |
|---|---|---|---|
| 10,079,999 B2 | 9/2018 | Van Den Brink | |
| 2001/0037666 A1* | 11/2001 | Roos | E05B 85/10 70/264 |

(Continued)

FOREIGN PATENT DOCUMENTS

| | | |
|---|---|---|
| CN | 105745922 A | 7/2016 |
| JP | 2014-236987 A | 12/2014 |

OTHER PUBLICATIONS

Combined Chinese Office Action and Search Report issued on Jul. 5, 2023 in Chinese Patent Application No. 202110669923.6, 7 pages.

*Primary Examiner* — Daniel Samwel
(74) *Attorney, Agent, or Firm* — Oblon, McClelland, Maier & Neustadt, L.L.P.

(57) ABSTRACT

A apparatus according to an embodiment includes a processing circuitry. The processing circuitry is configured to detect whether a mobile terminal is placed at a certain position that is located outside an entrance of a room in which a magnetic resonance imaging apparatus is installed. The processing circuitry is configured to execute unlock a door of the entrance, or output information related to permission for entry into the room through the entrance, in a case in which it is detected that the mobile terminal is placed at the certain position.

17 Claims, 9 Drawing Sheets

(56) References Cited

U.S. PATENT DOCUMENTS

| | | | |
|---|---|---|---|
| 2004/0135687 A1* | 7/2004 | Keene | G01V 11/00 |
| | | | 340/572.6 |
| 2007/0057786 A1* | 3/2007 | McClure | G01R 33/28 |
| | | | 340/551 |
| 2008/0242944 A1* | 10/2008 | Sharma | G16H 10/65 |
| | | | 600/300 |
| 2013/0285810 A1* | 10/2013 | Wooliscroft | G01V 11/00 |
| | | | 340/540 |
| 2014/0361770 A1 | 12/2014 | Dannels | |
| 2015/0033629 A1* | 2/2015 | Barwick | E06B 11/085 |
| | | | 49/13 |
| 2015/0329260 A1* | 11/2015 | Singh | G06Q 30/014 |
| | | | 705/28 |
| 2016/0097831 A1 | 4/2016 | Dannels et al. | |
| 2016/0295171 A1* | 10/2016 | Van Den Brink | G06V 20/52 |
| 2019/0154863 A1* | 5/2019 | Keene | G01R 33/288 |
| 2021/0103016 A1* | 4/2021 | Horton | G01R 33/288 |
| 2021/0247541 A1* | 8/2021 | Manneschi | G01V 3/165 |

* cited by examiner

# APPARATUS FOR UNLOCKING DOOR TO ROOM CONTAINING AN MRI APPARATUS

CROSS-REFERENCE TO RELATED APPLICATIONS

This application is based upon and claims the benefit of priority from Japanese Patent Application No. 2020-107219, filed on Jun. 22, 2020; the entire contents of which are incorporated herein by reference.

FIELD

Embodiments described herein and the drawings relate generally to an apparatus, a system, and a method.

BACKGROUND

In the related art, there is known magnetic resonance imaging (MRI) as a method of imaging a medical image. Magnetic resonance imaging is an imaging method of magnetically exciting nuclear spin of a subject placed in a static magnetic field by a radio frequency (RF) pulse of Larmor frequency of the nuclear spin, and generating an image from data of a magnetic resonance signal that is generated by the excitation. A high magnetic field is generated from a magnetic resonance imaging apparatus that performs such magnetic resonance imaging.

Due to this, when a magnetic body such as a metal product is carried into an imaging room in which the magnetic resonance imaging apparatus is installed, an adsorption accident may occur. For example, in recent years, a mobile terminal such as a portable tablet terminal is used in medical institutions in some cases, and such a mobile terminal may include a magnetic body.

DETAILED DESCRIPTION

The following describes embodiments of an apparatus, a system, and a computer program in detail with reference to the drawings.

First Embodiment

An apparatus according to an embodiment includes a processing circuitry. The processing circuitry is configured to detect whether a mobile terminal is placed at a certain position that is located outside an entrance of a room in which a magnetic resonance imaging apparatus is installed. The processing circuitry is configured to execute unlock a door of the entrance, or output information related to permission for entry into the room through the entrance, in a case in which it is detected that the mobile terminal is placed at the certain position.

Figure 1:
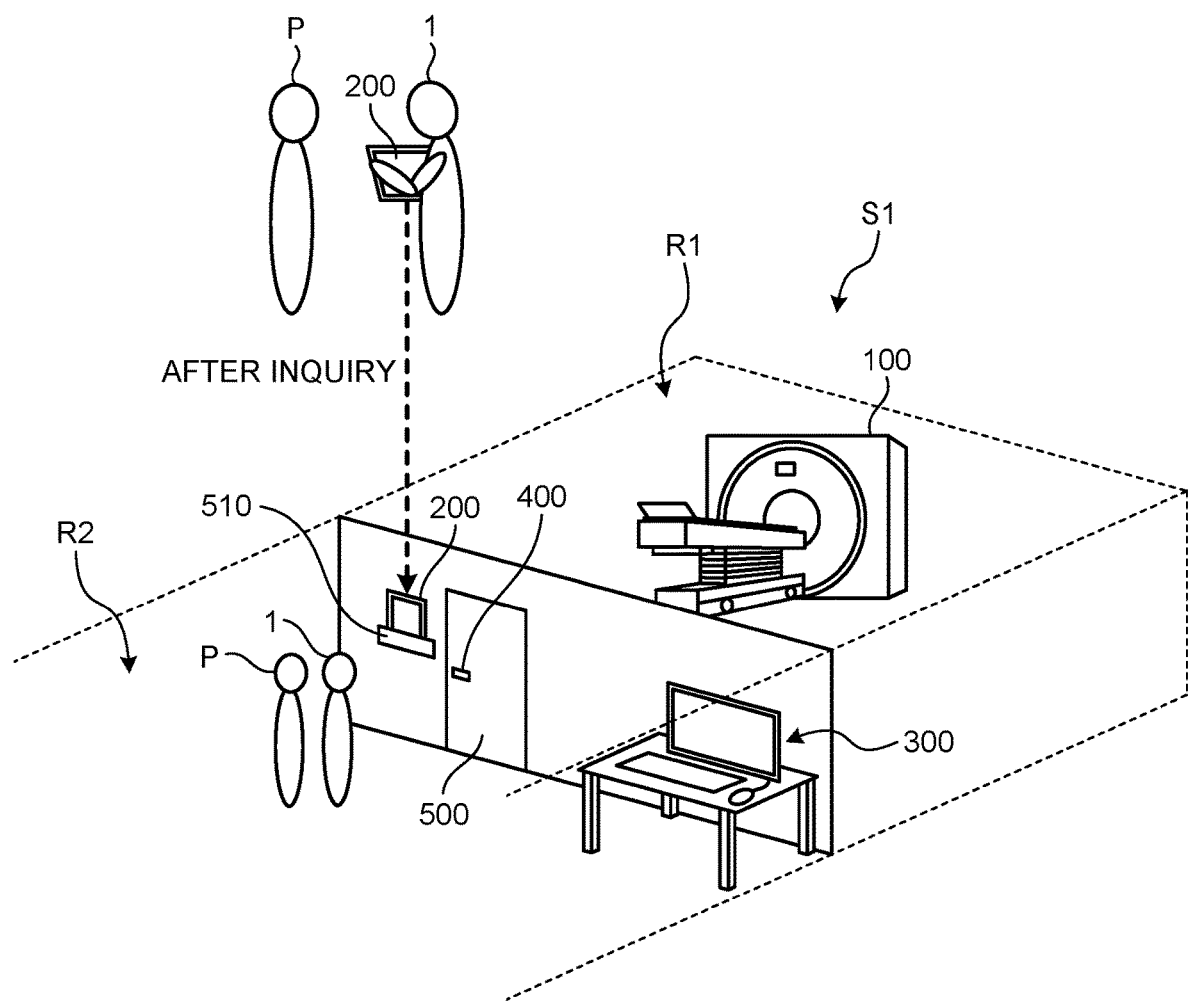
FIG. 1 is a diagram illustrating an example of an imaging room in which a magnetic resonance imaging apparatus according to a first embodiment is installed.

FIG. 1 is a diagram illustrating an example of an imaging room R1 in which a magnetic resonance imaging (MRI) apparatus 100 according to a first embodiment is installed.

An entry management system S1 according to the present embodiment includes the magnetic resonance imaging apparatus 100, a tablet terminal 200, an electric lock 400, and a tablet holder 510. The entry management system S1 is a system for managing entry of a technician 1 or a patient P into the imaging room R1. The entry management system S1 may also include another configuration. The tablet terminal 200 and the tablet holder 510 are not necessarily included in the entry management system S1. The entry management system S1 is an example of a system according to the present embodiment.

The magnetic resonance imaging apparatus 100 images the patient P by magnetic resonance imaging. Magnetic resonance imaging is an imaging method of magnetically exciting nuclear spin of a subject placed in a static magnetic field by a radio frequency (RF) pulse of Larmor frequency of the nuclear spin, and generating an image from data of a magnetic resonance signal that is generated following the excitation. Due to this, a high magnetic field is generated from the magnetic resonance imaging apparatus 100.

The imaging room R1 is a room in which the magnetic resonance imaging apparatus 100 is installed. The imaging room R1 is a shield room constructed to prevent external electromagnetic waves from entering the imaging room R1, and to confine electromagnetic waves generated from the magnetic resonance imaging apparatus 100 in the imaging room R1 so that the electromagnetic waves do not leak outside.

A door 500 of the entrance of the imaging room R1 is connected to an operation room R2. The patient P and the technician 1 enter the imaging room R1 through the door 500. The door 500 also serves as an exit from the imaging room R1. The technician 1 is an example of a health professional. The technician 1 according to the present embodiment may be replaced with another health professional such as a doctor or a nurse.

A positional relation between the imaging room R1 and the operation room R2 is not limited to the example illustrated in FIG. 1. For example, another exit and entrance connected to a room other than the operation room R2 or a corridor may be provided to the imaging room R1.

A console apparatus 300 connected to the magnetic resonance imaging apparatus 100 is installed in the operation room R2.

The console apparatus 300 is used for managing the magnetic resonance imaging apparatus 100. For example, the console apparatus 300 displays a magnetic resonance image taken by the magnetic resonance imaging apparatus 100. The console apparatus 300 transmits, to the magnetic resonance imaging apparatus 100, information such as an imaging condition for the magnetic resonance imaging apparatus 100 input by a user.

The electric lock 400 is disposed on the door 500 of the entrance of the imaging room R1. The electric lock 400 controls unlocking and locking of the door 500 under control of the magnetic resonance imaging apparatus 100. The electric lock 400 is a lock that can be locked and unlocked by an operation mechanism such as a solenoid or a motor disposed therein. The electric lock 400 includes an operation panel (not illustrated), for example, and has a configuration on which a locking operation can be manually performed by the technician 1. A method of manual locking is not limited to the method using the operation panel, and a knob, a switch, and the like on which a locking or unlocking operation can be performed may be disposed on the door 500, or in the vicinity of the door 500. The electric lock 400 outputs, to the magnetic resonance imaging apparatus 100, a locking/unlocking state, and an opening/closing state of the door 500 as a signal. The electric lock 400 is assumed to include an electronic lock.

The tablet terminal 200 is used when the technician 1 inquires of the patient P about his/her condition before the patient P is subjected to an examination by the magnetic resonance imaging apparatus 100. The tablet terminal 200 has a wireless communication function, and is communicably connected to a calculator system of the magnetic resonance imaging apparatus 100. In addition, the tablet terminal 200 is communicably connected to an information processing system in a medical institution, such as a hospital information system (HIS) or a radiology information system (RIS).

In the inquiry, the technician 1 confirms the identity of the patient P and explains the points to be noted about imaging with the magnetic resonance imaging apparatus 100, for example.

After the inquiring of the patient P, the technician 1 guides the patient P to the imaging room R1, and enters the imaging room R1 together with the patient P. The technician 1 then places the patient P on a couch of the magnetic resonance imaging apparatus 100, fixes a posture of the patient P, and sets a radio frequency (RF) coil.

The tablet terminal 200 is an example of the mobile terminal according to the present embodiment. The tablet terminal 200 may be part of the magnetic resonance imaging apparatus 100, or may be a separate apparatus from the magnetic resonance imaging apparatus 100. In a case in which the tablet terminal 200 is a separate apparatus from the magnetic resonance imaging apparatus 100, the tablet terminal 200 may be a versatile tablet terminal, for example. The mobile terminal is not limited to the tablet terminal 200, and may be a portable computer having a wireless communication function. For example, the mobile terminal may be a smartphone and the like.

The tablet holder 510 on which the tablet terminal 200 can be placed is disposed outside the door 500 of the entrance of the imaging room R1. The tablet holder 510 is disposed in the vicinity of the door 500, for example. The tablet holder 510 is an example of a certain position according to the present embodiment. The certain position is not limited to the tablet holder 510, and may be a stand and the like on which the tablet terminal 200 can be placed flat, for example.

The tablet holder 510 includes a connector electrically connected to the tablet terminal 200, for example. The connector is disposed at a position to be connected to an input/output terminal of the tablet terminal 200 in a case in which the tablet terminal 200 is placed on the tablet holder 510. In a case in which the connector is connected to the tablet terminal 200, the tablet holder 510 transmits, to the calculator system of the magnetic resonance imaging apparatus 100, a signal representing that the tablet terminal 200 is placed. The tablet terminal 200 is communicably connected to the calculator system (illustrated in FIG. 2) of the magnetic resonance imaging apparatus 100 via the connector of the tablet holder 510.

The tablet holder 510 may also have another function in addition to the role of connecting the calculator system of the magnetic resonance imaging apparatus 100 with the tablet terminal 200.

For example, the tablet holder 510 may also include a sensor for detecting that the tablet terminal 200 is placed. A detection method by the sensor is not specifically limited. In a case of detecting that the tablet terminal 200 is placed, the sensor transmits, to the calculator system of the magnetic resonance imaging apparatus 100, a signal representing that the tablet terminal 200 is placed. In a case of detecting that the tablet terminal 200 is removed from the tablet holder 510, the sensor may transmit, to the calculator system of the magnetic resonance imaging apparatus 100, a signal representing that the tablet terminal 200 is removed.

The tablet holder 510 may be configured as part of the electric lock 400.

The magnetic resonance imaging apparatus 100 according to the present embodiment controls locking and unlocking of the electric lock 400. More specifically, in a case in which the tablet terminal 200 is placed on the tablet holder 510, the magnetic resonance imaging apparatus 100 according to the present embodiment controls the electric lock 400 to be unlocked. The magnetic resonance imaging apparatus 100 is an example of the apparatus according to the present embodiment.

As illustrated in FIG. 1, the technician 1 places the tablet terminal 200 on the tablet holder 510 at the time of entering the imaging room R1. In this case, the electric lock 400 is unlocked, so that the technician 1 and the patient P can open the door 500 and enter the imaging room R1. That is, in the present embodiment, the technician 1 uses the tablet terminal 200 as a key for unlocking the door 500 of the imaging room R1.

In the present embodiment, in a case in which the door 500 is in a closed state and the tablet terminal 200 is not placed on the tablet holder 510, the electric lock 400 is assumed to be in a locked state. Thus, basically, unless the tablet terminal 200 is placed, the technician 1 cannot open the door 500, and cannot enter the imaging room R1. In a case in which the technician 1 or the patient P opens the door 500 from the inside of the imaging room R1, the electric lock 400 is unlocked irrespective of whether the tablet terminal 200 is placed on the tablet holder 510.

Next, the following describes a hardware configuration and a function of the magnetic resonance imaging apparatus 100 according to the present embodiment.

Figure 2:
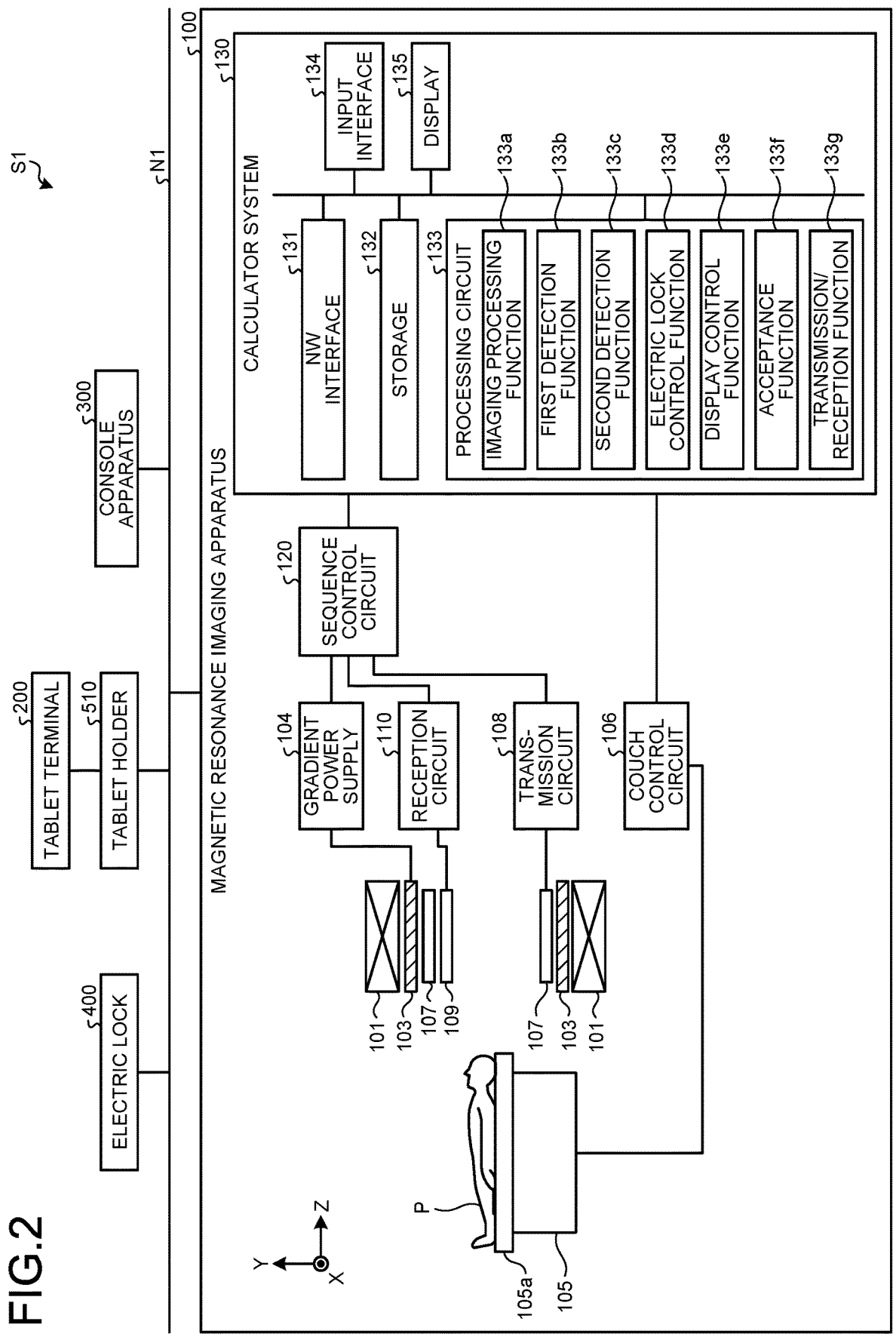
FIG. 2 is a block diagram illustrating an example of an entry management system including the magnetic resonance imaging apparatus according to the first embodiment.

FIG. 2 is a block diagram illustrating an example of the entry management system S1 including the magnetic resonance imaging apparatus 100 according to the first embodiment.

The magnetic resonance imaging apparatus 100, the electric lock 400, and the tablet holder 510 are connected to each other via a network N1 such as an in-hospital local area network (LAN). The magnetic resonance imaging apparatus 100, the electric lock 400, and the tablet holder 510 are connected to each other in a wired manner via a wired LAN, for example. The tablet terminal 200 is connected to the magnetic resonance imaging apparatus 100 or a medical information apparatus (not illustrated) via wireless communication. In a state of being connected to the tablet holder 510, the tablet terminal 200 may communicate with the magnetic resonance imaging apparatus 100 through the tablet holder 510. The connection method between appliances is not limited thereto. For example, the electric lock 400 and the tablet holder 510 may be connected to each other via a dedicated cable different from the network N1.

The network N1 may be further connected to an HIS, an RIS, or a server apparatus and the like installed in the medical institution in which the imaging room R1 is disposed.

As illustrated in FIG. 2, the magnetic resonance imaging apparatus 100 includes a static magnetic field magnet 101, a static magnetic field power supply (not illustrated), a gradient coil 103, a gradient power supply 104, a couch 105, a couch control circuit 106, a transmission coil 107, a transmission circuit 108, a reception coil 109, a reception circuit 110, a sequence control circuit 120, and a calculator system 130.

The configuration illustrated in FIG. 2 is merely an example. For example, the sequence control circuit 120 and respective parts in the calculator system 130 may be configured to be integrated with each other or separated from each other as appropriate. The patient P is not included in the magnetic resonance imaging apparatus 100.

The static magnetic field magnet 101 is a magnet that is formed in a hollow, substantially cylindrical shape, and that generates a static magnetic field in the internal space. The static magnetic field magnet 101 is, for example, a superconducting magnet or a permanent magnet. In a case in which the static magnetic field magnet 101 is a permanent magnet, the magnetic resonance imaging apparatus 100 does not necessarily include the static magnetic field power supply. The static magnetic field power supply may be separated from the magnetic resonance imaging apparatus 100.

The gradient coil 103 is a coil formed in a hollow, substantially cylindrical shape, and disposed on an inner side of the static magnetic field magnet 101. The gradient coil 103 generates a gradient magnetic field the magnetic field strength of which varies along X-, Y-, and Z-axes orthogonal to each other. The gradient power supply 104 supplies an electric current to the gradient coil 103 under control of the sequence control circuit 120.

The couch 105 includes a couchtop 105a on which the patient P is placed, and inserts the couchtop 105a into an imaging port in a state in which the patient P such as a patient is placed thereon under control of the couch control circuit 106. The couch control circuit 106 drives the couch 105 to move the couchtop 105a in a longitudinal direction and vertical direction under control of the calculator system 130.

The transmission coil 107 generates a high-frequency magnetic field by receiving the RF pulse supplied from the transmission circuit 108, and applies the high-frequency magnetic field to the patient P. The transmission circuit 108 supplies the RF pulse to the transmission coil 107 under control of the sequence control circuit 120.

The reception coil 109 is disposed on an inner side of the gradient coil 103, and receives a magnetic resonance (MR) signal that is generated from the patient P due to influence of the high-frequency magnetic field. The reception coil 109 outputs the received MR signal to the reception circuit 110. A configuration in which the reception coil 109 also serves as the transmission coil 107 may be employed.

The reception circuit 110 analog-digital (AD) converts the analog MR signal output from the reception coil 109 to generate MR data. The reception circuit 110 transmits the generated MR data to the sequence control circuit 120. AD conversion may be performed inside the reception coil 109. The reception circuit 110 can perform optional signal processing in addition to the AD conversion.

The sequence control circuit 120 drives the gradient power supply 104, the transmission circuit 108, and the reception circuit 110 to image the patient P based on sequence information transmitted from the calculator system 130. The sequence information is information defining a procedure for performing imaging. The sequence control circuit 120 may be implemented by a processor, or may be implemented by using software and hardware in combination.

After imaging the patient P by driving the gradient power supply 104, the transmission circuit 108, and the reception circuit 110, and receiving the MR data from the reception circuit 110, the sequence control circuit 120 transfers the received MR data to the calculator system 130.

The calculator system 130 controls the entire magnetic resonance imaging apparatus 100, and generates an MR image, for example. As illustrated in FIG. 2, the calculator system 130 includes a network (NW) interface 131, a storage circuit 132, a processing circuit 133, an input interface 134, and a display 135.

The storage circuit 132 stores the MR data received by the NW interface 131, k-space data disposed in a k-space by the processing circuit 133 (described later), image data generated by the processing circuit 133, and the like. The storage circuit 132 is, for example, a semiconductor memory element such as a random access memory (RAM) and a flash memory, a hard disk, or an optical disc.

The input interface 134 accepts various instructions and information inputs from an operator. The input interface 134 is, for example, implemented by a trackball, a switch button, a mouse, a keyboard, a touch pad for performing input operation by touching an operation surface, a touch screen obtained by integrating a display screen with a touch pad, a noncontact input circuit using an optical sensor, a voice input circuit, and the like. The input interface is connected to the processing circuit 133, and converts an input operation received from the operator into an electric signal to be output to the processing circuit 133. Herein, the input interfaces are not limited to those with physical operation parts such as a mouse or a keyboard. For example, examples of the input interface include a processing circuit for an electric signal that receives an electric signal corresponding to an input operation from an external input appliance that is disposed to be separated from the calculator system 130, and outputs the electric signal to a control circuit.

The display 135 displays various graphical user interfaces (GUIs), a guidance screen for the technician 1, a magnetic resonance image generated by the processing circuit 133, and the like under control of the processing circuit 133. The display 135 is, for example, a display device such as a liquid crystal display.

The processing circuit 133 controls the entire magnetic resonance imaging apparatus 100. More specifically, by way of example, the processing circuit 133 has an imaging processing function 133a, a first detection function 133b, a second detection function 133c, an electric lock control function 133d, a display control function 133e, an acceptance function 133f, and a transmission/reception function 133g. The imaging processing function 133a is an example of an imaging processing unit and a imaging processer. The first detection function 133b is an example of a first detection unit and a first detecter. The second detection function 133c is an example of a second detection unit and a second detecter. The electric lock control function 133d is an example of an entry management unit and an entry manager. Alternatively, both of the electric lock 400 and the electric lock control function 133d may be an example of the entry management unit and the entry manager. Furthermore, the electric lock 400 may be an example of the entry management unit and the entry manager. The display control function 133e is an example of a display control unit and a display controller. The acceptance function 133f is an example of an acceptance unit and an accepter. The transmission/reception function 133g is an example of a transmission/reception unit and a transmitter/recepter.

For example, each of processing functions including the imaging processing function 133a, the first detection function 133b, the second detection function 133c, the electric lock control function 133d, the display control function 133e, the acceptance function 133f, and the transmission/reception function 133g as constituent elements of the processing circuit 133 is stored in the storage circuit 132 as a computer-executable program. The processing circuit 133 is a processor. For example, the processing circuit 133 implements a function corresponding to each computer program by reading out the computer program from the storage circuit 132 to be executed. In other words, the processing circuit 133 that has read out the computer programs is assumed to have the respective functions illustrated in the processing circuit 133 in FIG. 2. In FIG. 2, the processing functions executed by the imaging processing function 133a, the first detection function 133b, the second detection function 133c, the electric lock control function 133d, the display control function 133e, the acceptance function 133f, and the transmission/reception function 133g are assumed to be implemented by a single processor, but the processing circuit 133 may be configured by combining a plurality of independent processors, and each of the processors may execute the computer program to implement the function. In FIG. 2, the single storage circuit 132 is assumed to store computer programs corresponding to the respective processing functions, but the configuration may be made such that a plurality of storage circuits may be disposed in a distributed manner, and the processing circuit 133 may read out a corresponding computer program from an individual storage circuit.

The imaging processing function 133a controls the parts of the magnetic resonance imaging apparatus 100 to perform imaging of a magnetic resonance image. More specifically, the imaging processing function 133a generates sequence information, collects MR data, generates k-space data, and generates the magnetic resonance image. The imaging processing function 133a stores the generated magnetic resonance image in the storage circuit 132, for example.

The first detection function 133b detects whether the tablet terminal 200 is placed on the tablet holder 510 that is disposed outside the entrance of the imaging room R1 in which the magnetic resonance imaging apparatus 100 is installed.

More specifically, in a case in which the tablet terminal 200 is placed on the tablet holder 510, the first detection function 133b acquires a signal indicating that the tablet terminal 200 is placed from the tablet holder 510 via the wired network N1 and the NW interface 131 to detect that the tablet terminal 200 is placed.

The first detection function 133b, while connected to the tablet terminal 200 via the connector of the tablet holder 510 and the wired network N1, determines that the tablet terminal 200 is placed on the tablet holder 510. In a case in which wired connection with the tablet terminal 200 is in a disconnected state, the first detection function 133b determines that the tablet terminal 200 is not placed on the tablet holder 510. The method of determining whether the tablet terminal 200 is placed on the tablet holder 510 is not limited thereto. The first detection function 133b may acquire, from the sensor disposed on the tablet holder 510, a signal representing that the tablet terminal 200 is placed or removed, for example.

The first detection function 133b sends out a detection result indicating whether the tablet terminal 200 is placed on the tablet holder 510 to the electric lock control function 133d.

The second detection function 133c detects the locking state of the electric lock 400 and the opening/closing state of the door 500 by acquiring the locking/unlocking state, and the opening/closing state of the door 500 from the electric lock 400 as a signal via the wired network N1 and the NW interface 131. The second detection function 133c sends out, to the electric lock control function 133d, a detection result of the locking state of the electric lock 400 and the opening/closing state of the door 500.

In a case in which it is detected that the tablet terminal 200 is placed on the tablet holder 510, the electric lock control function 133d outputs information related to unlocking of the door 500 of the entrance or permission for entry through the entrance. In the present embodiment, the electric lock control function 133d unlocks the door 500 of the entrance of the imaging room R1 in a case in which it is detected that the tablet terminal 200 is placed. For example, the electric lock control function 133d unlocks the door 500 of the entrance by transmitting a control signal for instructing unlocking to the electric lock 400 via the network N1 and the NW interface 131.

In a period in which the tablet terminal 200 is placed on the tablet holder 510, the electric lock control function 133d keeps the door 500 in the unlocked state. Due to this, after the technician 1 unlocks the door 500 by placing the tablet terminal 200 on the tablet holder 510 at the time of entering the room, time and effort are reduced for unlocking the door 500 every time the technician 1 enters or exits from the imaging room R1 through the door 500 for work. The electric lock control function 133d may permit the technician 1 to manually operate the electric lock 400 to be in the locked state.

In a case in which the door 500 is in the closed state and the tablet terminal 200 is removed from the tablet holder 510, the electric lock control function 133d locks the door 500 of the entrance.

The electric lock control function 133d enables the door 500 to be opened from the inside of the imaging room R1 irrespective of whether the tablet terminal 200 is placed on the tablet holder 510. For example, in a case in which a doorknob of the door 500 inside the imaging room R1 is operated by the technician 1, the electric lock control function 133d controls the electric lock 400 to be unlocked.

That is, in a case in which the door 500 is in the locked state, the technician 1 or the patient P cannot open the door 500 from the outside of the imaging room R1, but can open the door 500 from the inside of the imaging room R1. The function of enabling the door 500 to be opened from the inside of the imaging room R1 is not limited to the electric lock control function 133d, and may be a function implemented by the electric lock 400.

The display control function 133e causes the display 135 to display the magnetic resonance image generated by the imaging processing function 133a. The display control function 133e also causes the display 135 to display various GUIs.

The acceptance function 133f accepts various operations performed by the technician 1 via the input interface 134.

The transmission/reception function 133g transmits/receives information to/from the console apparatus 300 via the network N1 and the NW interface 131. For example, the transmission/reception function 133g transmits the magnetic resonance image generated by the imaging processing function 133a to the console apparatus 300. The transmission/reception function 133g also receives, from the console apparatus 300, information such as an imaging condition input through the console apparatus 300.

The console apparatus 300 is, for example, a personal computer (PC) including a storage circuit, a processing circuit such as a CPU, an NW interface, an input interface, a display, and the like.

The tablet terminal 200 includes, for example, a storage circuit, a processing circuit such as a CPU, an NW interface, an input interface, a display, a camera, and the like. The input interface of the tablet terminal 200 is assumed to be a touch screen obtained by integrating a display with a touch pad.

As described above with reference to FIG. 1, for example, the tablet terminal 200 is used for inquiring of the patient P about his/her condition by the technician 1 before the patient P is subjected to an examination by the magnetic resonance imaging apparatus 100.

Figure 3:
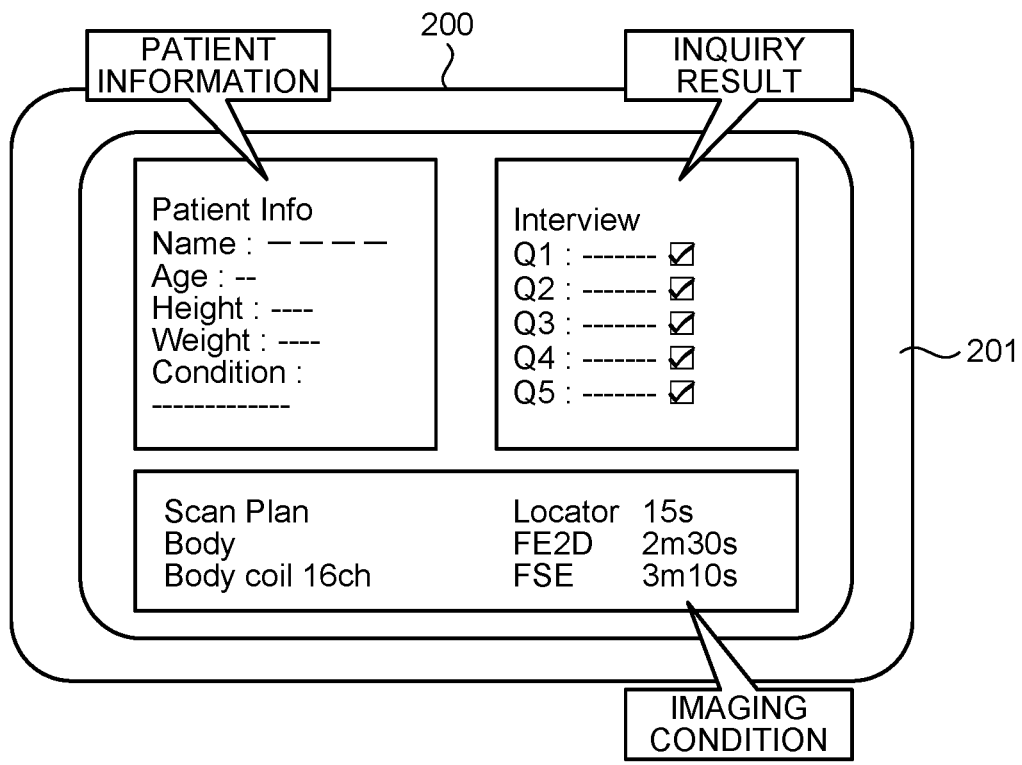
FIG. 3 is a diagram illustrating an example of an inquiry screen displayed on a tablet terminal according to the first embodiment.

FIG. 3 is a diagram illustrating an example of an inquiry screen displayed on the tablet terminal 200 according to the first embodiment. As illustrated in FIG. 3, patient information of the patient P, an inquiry result, and an imaging condition for MRI imaging of the patient P are displayed on a display 201 of the tablet terminal 200. The patient information includes, for example, a name, an age, a height, a body weight, a symptom of the patient P, and the like. The patient information and the imaging condition are acquired by the tablet terminal 200 from an HIS, an RIS, or the magnetic resonance imaging apparatus 100 to be displayed on the display 201, for example. The technician 1 inputs, to the tablet terminal 200, content that is heard from the patient P at the time of inquiring of the patient P as the inquiry result.

In the above description, described is an example in which the "processor" reads out a computer program corresponding to each function from the storage circuit to be executed, but the embodiment is not limited thereto. The word "processor" means, for example, a circuit such as a central processing unit (CPU), a graphics processing unit (GPU), an application specific integrated circuit (ASIC), and a programmable logic device (for example, a simple programmable logic device (SPLD), a complex programmable logic device (CPLD), and a field programmable gate array (FPGA)). In a case in which the processor is a CPU, for example, the processor implements a function by reading out a computer program stored in the storage circuit to be executed. On the other hand, in a case in which the processor is an ASIC, the function is directly incorporated in a circuit of the processor as a logic circuit instead of storing a computer program in the storage circuit. Each processor of the present embodiment is not necessarily configured as a single circuit, and the function thereof may be implemented by combining a plurality of independent circuits to be configured as one processor. Additionally, the function may be implemented by integrating a plurality of constituent elements in FIG. 2 into one processor.

Next, the following describes a procedure of entry/exit management processing for the imaging room R1 performed by the magnetic resonance imaging apparatus 100 according to the present embodiment configured as described above.

Figure 4:
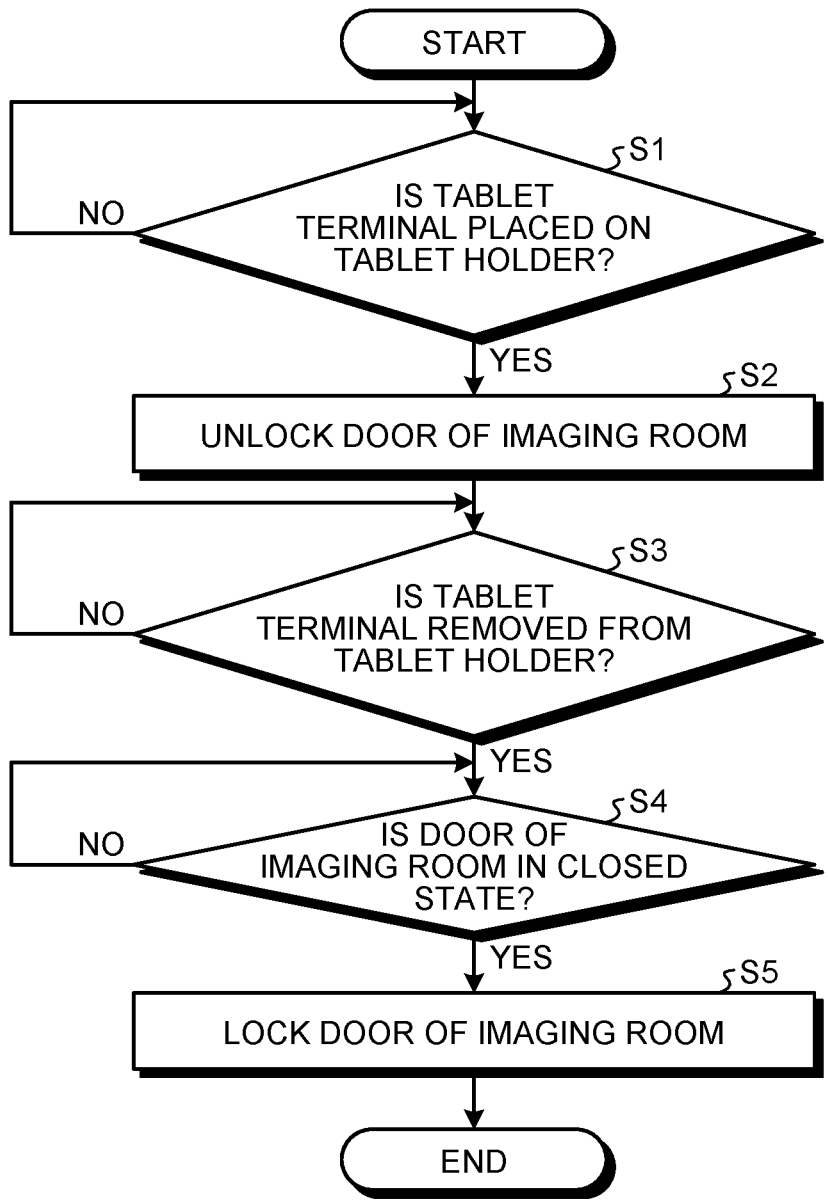
FIG. 4 is a flowchart illustrating an example of a procedure of entry management processing according to the first embodiment.

FIG. 4 is a flowchart illustrating an example of a procedure of entry management processing according to the first embodiment. At the time when the processing is started in this flowchart, the door 500 of the imaging room R1 is assumed to be in the closed state, and is locked. At the time when the processing is started in this flowchart, the technician 1 and the patient P are assumed to be present outside the imaging room R1.

First, the first detection function 133b determines whether it is detected that the tablet terminal 200 is placed on the tablet holder 510 (S1). If the first detection function 133b determines that it is not detected that the tablet terminal 200 is placed on the tablet holder 510 (No at S1), the processing at S1 is repeated.

If the first detection function 133b determines that it is detected that the tablet terminal 200 is placed on the tablet holder 510 (Yes at S1), the electric lock control function 133d controls the electric lock 400 to unlock the door 500 of the imaging room R1 (S2).

At this point, the technician 1 and the patient P open the unlocked door 500 and enter the imaging room R1. After entering the room, the technician 1 causes the door 500 to be in the closed state. The technician 1 places the patient P on the couch 105, fixes the posture of the patient P, and sets the radio frequency (RF) coil. The technician 1 then performs imaging by the magnetic resonance imaging apparatus 100. In this flowchart, the imaging processing is omitted.

The first detection function 133b determines whether the tablet terminal 200 is removed from the tablet holder 510 (S3).

For example, in a period in which the first detection function 133b is connected to the tablet terminal 200 via the connector of the tablet holder 510 and the wired network N1, the first detection function 133b determines that the tablet terminal 200 is not removed from the tablet holder 510 (No at S3). In this case, the first detection function 133b repeats the processing at S3.

For example, if it is detected that wired connection with the tablet terminal 200 is in the disconnected state, the first detection function 133b determines that the tablet terminal 200 is removed from the tablet holder 510 (Yes at S3).

The second detection function 133c acquires the opening/closing state of the door 500 from the electric lock 400, and determines whether the door 500 is in the closed state (S4). If it is determined that the door 500 is in the opened state (No at S4), the second detection function 133c repeats the processing at S4.

If the second detection function 133c determines that the door 500 is in the closed state (Yes at S4), the electric lock control function 133d controls the electric lock 400 to lock the door 500 of the imaging room R1 (S5).

The electric lock control function 133d may transmit, to the electric lock 400, a control signal for instructing to lock the door 500 of the imaging room R1 irrespective of whether the door 500 is in the closed state. In this case, the electric lock 400 locks the door 500 at a timing when the door 500 is caused to be in the closed state after receiving the control signal for instructing to lock the door 500 of the imaging room R1.

At this point, the processing of this flowchart ends. The processing of the flowchart is repeatedly performed in a period in which the magnetic resonance imaging apparatus 100 is working.

As described above, the magnetic resonance imaging apparatus 100 according to the present embodiment unlocks the door 500 of the entrance in a case in which it is detected that the tablet terminal 200 is placed on the tablet holder 510 that is disposed outside the entrance of the imaging room R1 in which the magnetic resonance imaging apparatus 100 is installed. That is, the technician 1 cannot enter the imaging room R1 unless the technician 1 places the tablet terminal 200 outside the entrance of the imaging room R1. Thus, the magnetic resonance imaging apparatus 100 according to the present embodiment can reduce a case in which the technician 1 accidentally carries the tablet terminal 200 into the imaging room R1 in which the magnetic resonance imaging apparatus 100 is installed.

For example, in a case in which a magnetic body such as metal is used for the tablet terminal, an adsorption accident may occur when the technician enters the imaging room while having the tablet terminal that has been used for an inquiry. In a case where a tablet terminal not including a magnetic body is used to prevent the adsorption accident from occurring, it becomes difficult to use a typical tablet terminal for an inquiry and the like. On the other hand, in the present embodiment, the tablet terminal 200 is used as a key for unlocking the door 500 of the imaging room R1, and the technician 1 enters the imaging room R1 after placing the tablet terminal 200 on the tablet holder 510, so that it is possible to reduce the adsorption accident that occurs when the technician 1 enters the imaging room R1 while having the tablet terminal 200.

Furthermore, for example, it may be difficult for the technician 1 to support the patient while holding the tablet terminal, so that time and effort are required for temporarily placing the tablet terminal in some cases. On the other hand, according to the present embodiment, the tablet holder 510 is prepared outside the entrance of the imaging room R1, so that the technician 1 can leave the tablet terminal 200 immediately before entering the imaging room R1, and can smoothly support the patient P who enters the imaging room R1.

In the present embodiment, the tablet terminal 200 and the magnetic resonance imaging apparatus 100 are assumed to communicate with each other, but the tablet terminal 200 does not necessarily include a unit for communicating with the magnetic resonance imaging apparatus 100 or software thereof.

Second Embodiment

In the first embodiment described above, the magnetic resonance imaging apparatus 100 controls locking and unlocking of the door 500 of the entrance for managing entry of the technician 1 and the patient P into the imaging room R1, but the method of managing entry is not limited thereto. In a second embodiment, the magnetic resonance imaging apparatus 100 manages entry into the imaging room R1 by outputting information related to permission for entry into the imaging room R1 through the entrance.

Figure 5:
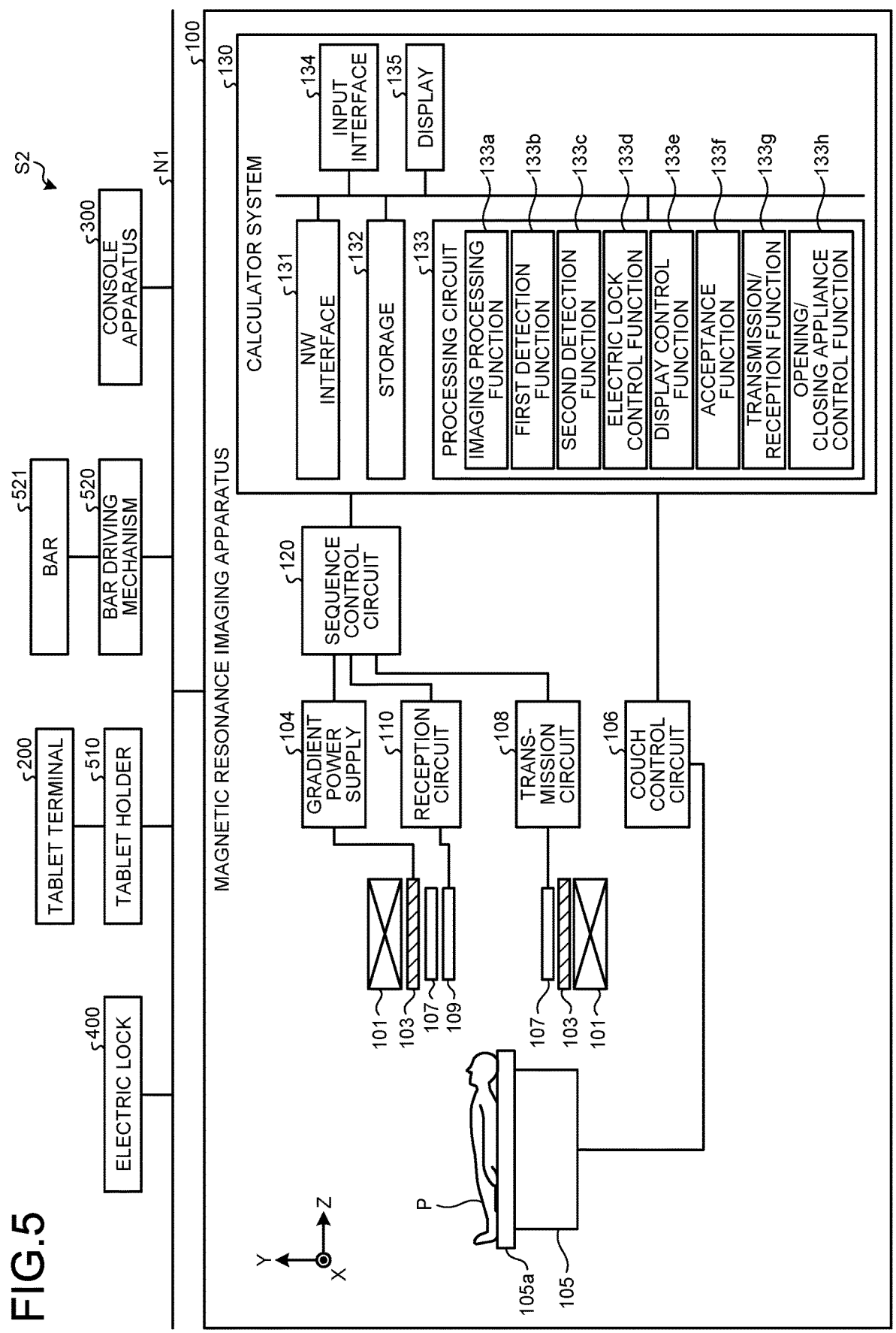
FIG. 5 is a block diagram illustrating an example of an entry management system including a magnetic resonance imaging apparatus according to a second embodiment.

FIG. 5 is a block diagram illustrating an example of an entry management system S2 including the magnetic resonance imaging apparatus 100 according to the second embodiment.

In the present embodiment, by way of example, a bar 521 that can be moved vertically or horizontally is assumed to be disposed outside the door 500 of the entrance of the imaging room R1. The bar 521 blocks or allows passage of the technician 1 or the patient P coming from the outside of the imaging room R1 toward the door 500 by being moved vertically or horizontally by a bar driving mechanism 520. For example, the bar 521 may be opened or closed similarly to a crossing gate of a railroad crossing.

The bar driving mechanism 520 includes a motor and an actuator, for example, and moves the bar 521 under control of the magnetic resonance imaging apparatus 100. The bar driving mechanism 520 may be connected to the magnetic resonance imaging apparatus 100 via the network N1 or a dedicated cable.

The configuration of the magnetic resonance imaging apparatus 100 according to the present embodiment is the same as the configuration in the first embodiment described above with reference to FIG. 2. The processing circuit 133 of the magnetic resonance imaging apparatus 100 according to the present embodiment has the imaging processing function 133a, the first detection function 133b, the second detection function 133c, the electric lock control function 133d, the display control function 133e, the acceptance function 133f, the transmission/reception function 133g, and an opening/closing appliance control function 133h. The opening/closing appliance control function 133h is an example of the entry management unit and the entry manager according to the present embodiment. The magnetic resonance imaging apparatus 100 is an example of the apparatus according to the present embodiment.

The imaging processing function 133a, the first detection function 133b, the second detection function 133c, the electric lock control function 133d, the display control function 133e, the acceptance function 133f, and the transmission/reception function 133g according to the present embodiment each have the same function as that in the first embodiment.

The opening/closing appliance control function 133h according to the present embodiment outputs information related to permission for entry into the imaging room R1 through the entrance in a case in which it is detected that the tablet terminal 200 is placed on the tablet holder 510.

More specifically, in a case in which it is detected that the tablet terminal 200 is placed on the tablet holder 510, the opening/closing appliance control function 133h according to the present embodiment enables passage of the technician 1 or the patient P coming from the outside of the imaging room R1 toward the door 500 by transmitting a control signal to the bar driving mechanism 520 that is disposed outside the door 500 of the entrance of the imaging room R1, and controlling the bar 521 to move from the front of the door 500. Transmission of the control signal is an example of output of the information related to permission for entry into the imaging room R1 through the entrance according to the present embodiment.

In the present embodiment, in a case in which the tablet terminal 200 is not placed on the tablet holder 510, the bar 521 is assumed to be positioned in front of the door 500 to block passage of the technician 1 or the patient P coming from the outside of the imaging room R1 toward the door 500. That is, in the present embodiment, the technician 1 uses the tablet terminal 200 as a key for moving the bar 521 from the front of the door 500.

As described above, in the magnetic resonance imaging apparatus 100 according to the present embodiment, the control signal is transmitted to move the bar 521 from the front of the door 500 in a case in which it is detected that the tablet terminal 200 is placed on the tablet holder 510. Thus, with the magnetic resonance imaging apparatus 100 according to the present embodiment, the tablet terminal 200 is used as a key for moving the bar 521 from the front of the door 500, so that it is possible to reduce a case in which the technician 1 accidentally carries the tablet terminal 200 into the imaging room R1 in which the magnetic resonance imaging apparatus 100 is installed. For example, the configuration according to the present embodiment can be applied to a case in which a function of an existing key of the door 500 is difficult to be changed.

In the present embodiment, the electric lock 400 is not necessarily disposed in the door 500 of the imaging room R1. Additionally, the magnetic resonance imaging apparatus 100 does not necessarily have the electric lock control function 133d.

Alternatively, the bar 521 according to the present embodiment may be configured as part of the electric lock 400. In a case of employing this configuration, the electric lock control function 133d is assumed to also serve as the opening/closing appliance control function 133h.

An opening/closing appliance other than the bar 521 may be employed. For example, a flap door, a movable fence, and the like may be disposed in front of the door 500.

Third Embodiment

In a third embodiment, the magnetic resonance imaging apparatus 100 causes a notification device to notify the patient P who enters the imaging room R1 of precautions related to a high magnetic field generated from the magnetic resonance imaging apparatus 100.

Figure 6:
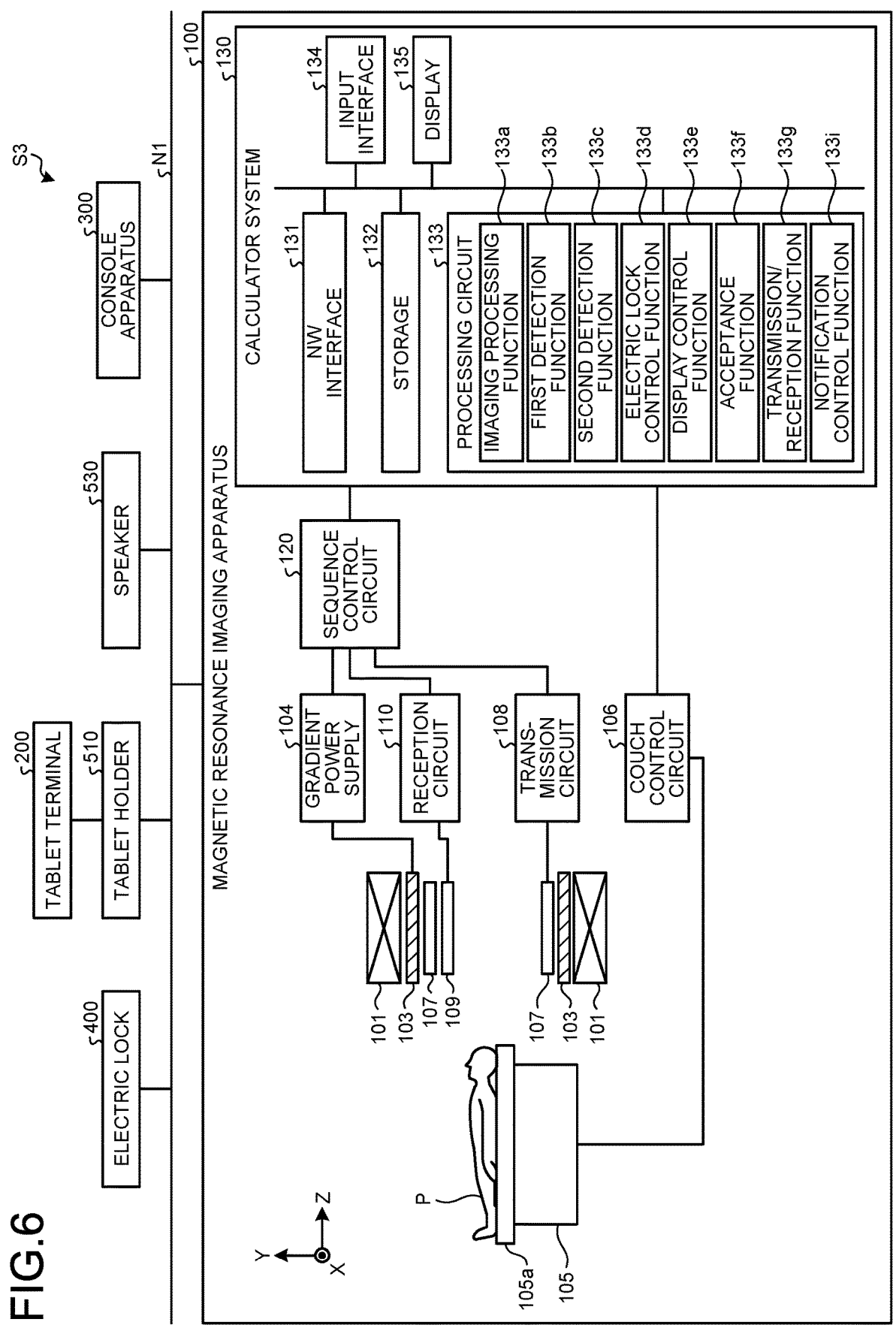
FIG. 6 is a block diagram illustrating an example of an entry management system including a magnetic resonance imaging apparatus according to a third embodiment.

FIG. 6 is a block diagram illustrating an example of an entry management system S3 including the magnetic resonance imaging apparatus 100 according to the third embodiment.

In the present embodiment, a speaker 530 is disposed outside the door 500 of the imaging room R1. The speaker 530 is disposed in the vicinity of the door 500. For example, the speaker 530 may be disposed on the tablet holder 510.

In a case in which it is detected that the tablet terminal 200 is placed on the tablet holder 510, before the door 500 of the entrance is unlocked or the information related to permission for entry into the imaging room R1 through the entrance is output, the speaker 530 notifies precautions related to a high magnetic field generated from the magnetic resonance imaging apparatus 100 under control of the magnetic resonance imaging apparatus 100. The speaker 530 is an example of the notification device according to the present embodiment.

The precautions related to a high magnetic field generated from the magnetic resonance imaging apparatus 100 are, for example, voice guidance that reads aloud that the imaging room R1 is under high magnetic field environment, an RF pulse is emitted at the time of imaging, a magnetic body such as metal should not be carried at the time of entering the imaging room R1, and the like. Content of the precautions is not limited thereto.

The configuration of the magnetic resonance imaging apparatus 100 according to the present embodiment is the same as the configuration in the first embodiment described above with reference to FIG. 2. The processing circuit 133 of the magnetic resonance imaging apparatus 100 according to the present embodiment includes the imaging processing function 133a, the first detection function 133b, the second detection function 133c, the electric lock control function 133d, the display control function 133e, the acceptance function 133f, the transmission/reception function 133g, and a notification control function 133i. The notification control function 133i is an example of a notification control unit and a notification controller. The magnetic resonance imaging apparatus 100 is an example of the apparatus according to the present embodiment.

The imaging processing function 133a, the first detection function 133b, the second detection function 133c, the electric lock control function 133d, the display control function 133e, the acceptance function 133f, and the transmission/reception function 133g according to the present embodiment each have the same function as that in the first embodiment.

In a case in which it is detected that the tablet terminal 200 is placed on the tablet holder 510, the notification control function 133i causes the speaker 530 to notify the precautions related to a high magnetic field generated from the magnetic resonance imaging apparatus 100 before the door 500 is unlocked by the electric lock control function 133d.

For example, by controlling the speaker 530 via the NW interface 131 and the network N1, the notification control function 133i causes the speaker 530 to notify the precautions related to a high magnetic field generated from the magnetic resonance imaging apparatus 100 as voice guidance.

As described above, in a case in which it is detected that the tablet terminal 200 is placed on the tablet holder 510, the magnetic resonance imaging apparatus 100 according to the present embodiment causes the speaker 530 to notify the precautions related to a high magnetic field generated from the magnetic resonance imaging apparatus 100 before the door 500 is unlocked by the electric lock control function 133d. Due to this, with the magnetic resonance imaging apparatus 100 according to the present embodiment, in addition to the effect of the first embodiment, it is possible to call attention of the technician 1 and the patient P immediately before the technician 1 and the patient P enter the imaging room R1, and reduce the risk of accidents caused by the technician 1 or the patient P accidentally carrying a magnetic body into the imaging room R1, for example.

In the present embodiment, the description has been made on the assumption that the electric lock control function 133d unlocks the door 500 in a case in which it is detected that the tablet terminal 200 is placed on the tablet holder 510, but the configuration according to the present embodiment may be applied to the configuration described in the second embodiment.

For example, as in the second embodiment described above, in a case in which the opening/closing appliance control function 133h outputs the information related to permission for entry into the imaging room R1 through the entrance when it is detected that the tablet terminal 200 is placed on the tablet holder 510, the notification control function 133i may cause the speaker 530 to notify the precautions related to a high magnetic field generated from the magnetic resonance imaging apparatus 100 before the information is output.

The notification device is not limited to the speaker 530. For example, a display may be disposed as the notification device outside the door 500 of the entrance of the imaging room R1. The display may be configured integrally with the tablet holder 510. In this case, the notification control function 133i may cause the display to display the precautions related to a high magnetic field generated from the magnetic resonance imaging apparatus 100 as character information or an image. The display and the speaker 530 may be integrally configured.

The tablet terminal 200 may function as the notification device. In this case, the notification control function 133*i* may cause the display 201 of the tablet terminal 200 to display the precautions related to a high magnetic field generated from the magnetic resonance imaging apparatus 100 as character information or an image. The notification control function 133*i* may cause a speaker of the tablet terminal 200 to output the precautions by voice.

Alternatively, a camera that can image the technician 1 and the patient P positioned in front of the door 500 may be disposed outside the door 500 of the entrance of the imaging room R1. For example, the notification control function 133*i* may detect structures such as an intravenous drip stand and a stretcher from a taken image acquired from the camera, and cause the speaker 530 or another notification device to notify announcement for urging the technician 1 or the patient P to check whether the detected structures do not include a magnetic body. The camera may be a camera included in the tablet terminal 200.

The structure as a detection target may be a structure including a magnetic body with high possibility, and registered in the storage circuit 132 in advance. As the method of detecting the structures such as an intravenous drip stand and a stretcher from the taken image, well-known image recognition processing, machine learning, and the like may be employed.

Fourth Embodiment

In a fourth embodiment, the magnetic resonance imaging apparatus 100 also authenticates the technician 1 or the patient P who enters the imaging room R1.

Figure 7:
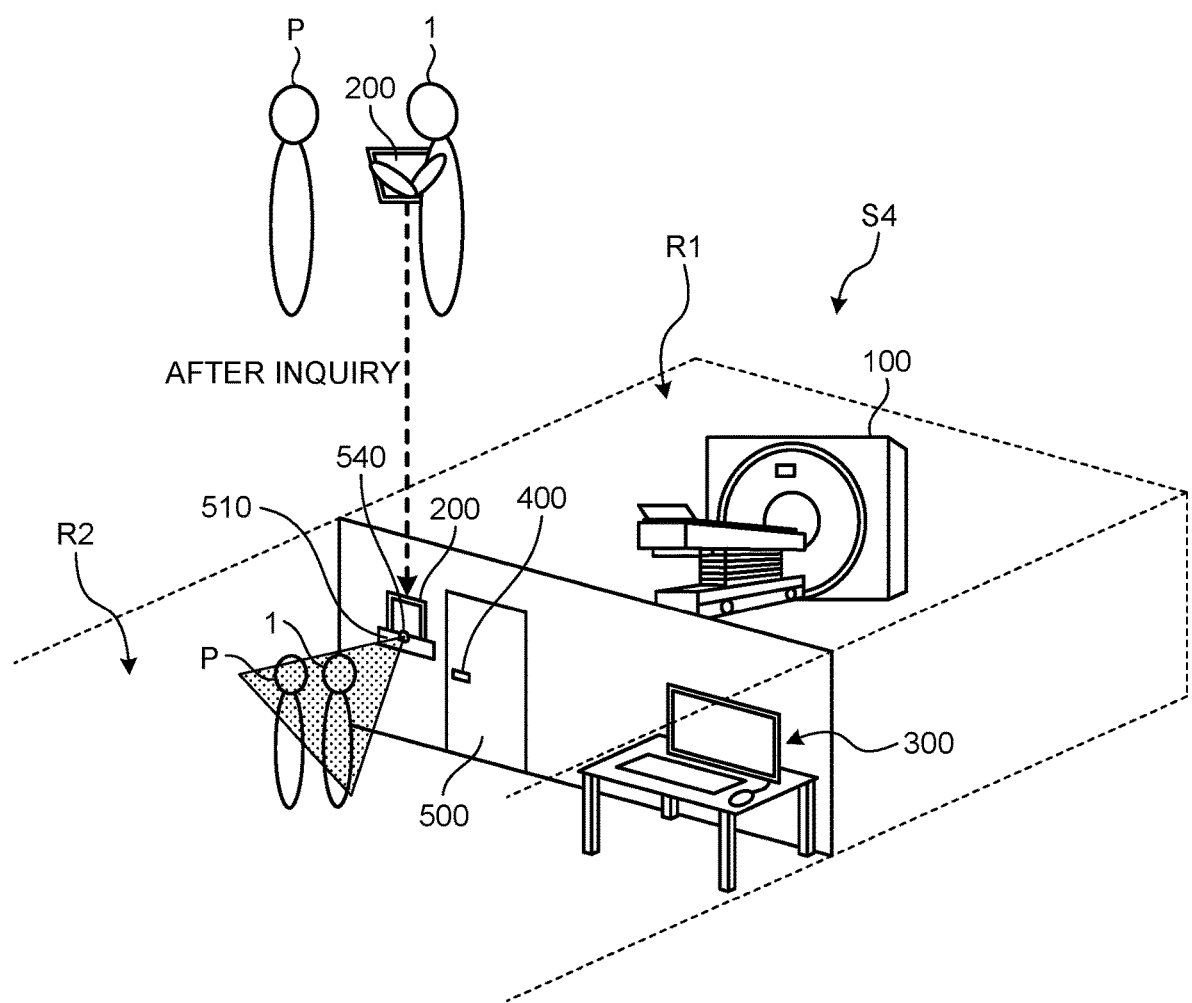
FIG. 7 is a diagram illustrating an example of an imaging room in which a magnetic resonance imaging apparatus according to a fourth embodiment is installed.

FIG. 7 is a diagram illustrating an example of the imaging room R1 in which the magnetic resonance imaging apparatus 100 according to the fourth embodiment is installed. The present embodiment describes face authentication as an example of an authentication method. As illustrated in FIG. 7, in the present embodiment, a camera 540 for imaging a face of the technician 1 or the patient P is disposed outside the door 500 of the entrance of the imaging room R1.

The camera 540 images a face of at least one of the technician 1 and the patient P. In a case in which a plurality of technicians are present in front of the door 500, the camera 540 may image a face of any one of the technicians, or may image faces of all the technicians.

In FIG. 7, the camera 540 is disposed on the tablet holder 510, but the camera 540 may be installed in the vicinity of the door 500, and the installation position is not limited to the example illustrated in FIG. 7. The camera 540 may be connected to the magnetic resonance imaging apparatus 100 via the network N1 or a dedicated cable.

For example, a camera included in the tablet terminal 200 may be employed in place of the camera 540.

Figure 8:
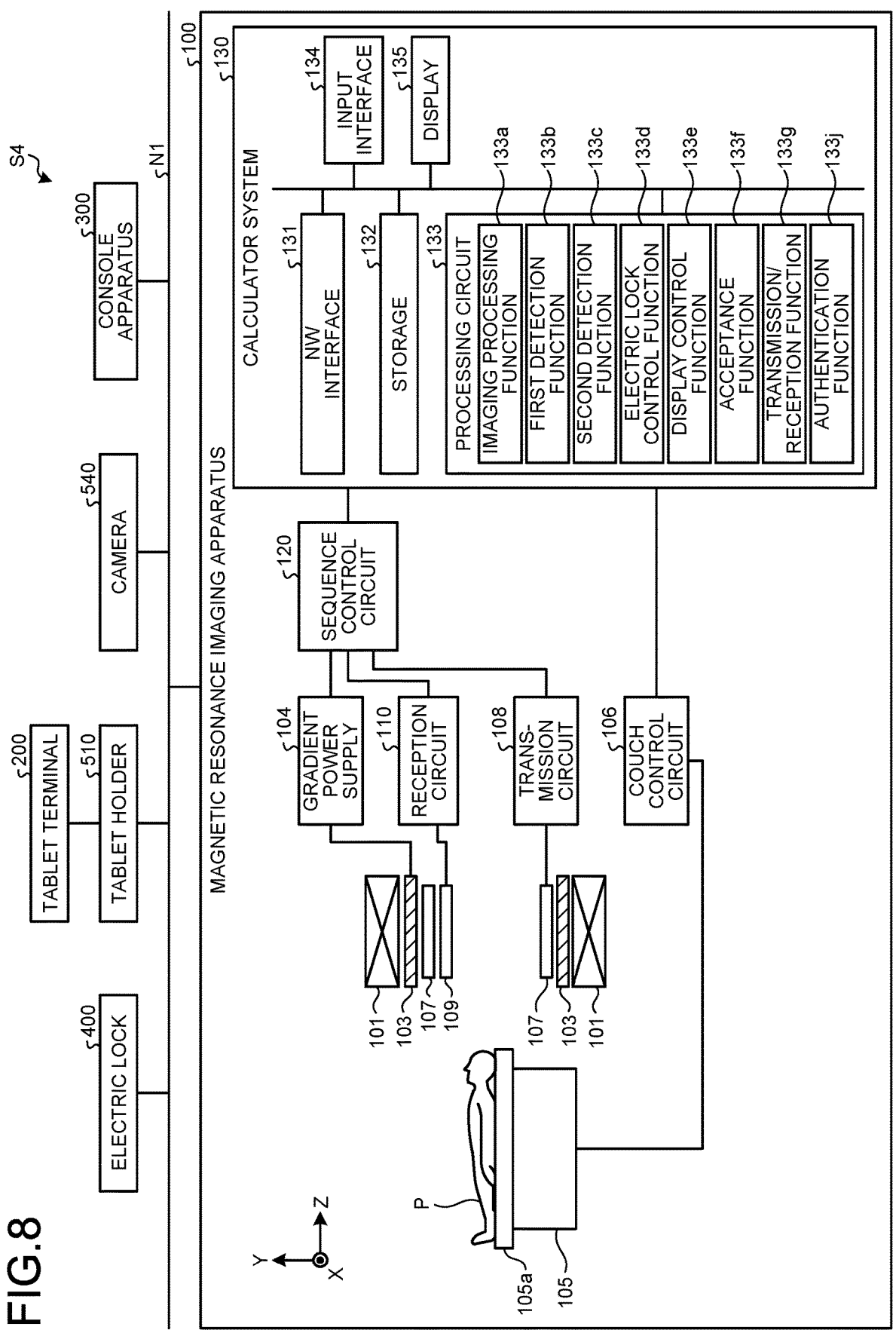
FIG. 8 is a block diagram illustrating an example of an entry management system including the magnetic resonance imaging apparatus according to the fourth embodiment.

FIG. 8 is a block diagram illustrating an example of an entry management system S4 including the magnetic resonance imaging apparatus 100 according to the fourth embodiment.

The storage circuit of the tablet terminal 200 according to the present embodiment stores identification information of the technician 1 who uses the tablet terminal 200, and identification information of the patient P as an inquiry target. The patient P as an inquiry target is a patient who has reserved examination by the magnetic resonance imaging apparatus 100. Pieces of the identification information include, for example, an ID number, a name, and the like.

For example, when being placed on the tablet holder 510, the tablet terminal 200 transmits, to the magnetic resonance imaging apparatus 100, the identification information of the technician 1 who uses the tablet terminal 200 and the identification information of the patient P as an inquiry target via the tablet holder 510 and the network N1. The timing and the method for transmitting the identification information of the technician 1 and the identification information of the patient P as an inquiry target are not limited thereto.

The configuration of the magnetic resonance imaging apparatus 100 according to the present embodiment is the same as the configuration in the first embodiment described above with reference to FIG. 2. The processing circuit 133 of the magnetic resonance imaging apparatus 100 according to the present embodiment has the imaging processing function 133*a*, the first detection function 133*b*, the second detection function 133*c*, the electric lock control function 133*d*, the display control function 133*e*, the acceptance function 133*f*, the transmission/reception function 133*g*, and an authentication function 133*j*. The authentication function 133*j* is an example of an authentication unit and an authenticator. The magnetic resonance imaging apparatus 100 is an example of the apparatus according to the present embodiment. The electric lock control function 133*d* is an example of the entry management unit according to the present embodiment.

The imaging processing function 133*a*, the first detection function 133*b*, the second detection function 133*c*, the display control function 133*e*, the acceptance function 133*f*, and the transmission/reception function 133*g* according to the present embodiment each have the same function as that in the first embodiment.

In a case in which it is detected that the tablet terminal 200 is placed on the tablet holder 510, the authentication function 133*j* authenticates at least one of the technician 1 and the patient P who are present outside the imaging room R1. The outside of the imaging room R1 is, for example, the front of the entrance of the imaging room R1, but is not limited thereto.

More specifically, the authentication function 133*j* according to the present embodiment compares the identification information of the technician 1 or the patient P that is specified from the taken image acquired from the camera 540 with the identification information of the technician 1 or the patient P registered in the tablet terminal 200. In a case in which the pieces of identification information match each other, the authentication function 133*j* authenticates the technician 1 or the patient P depicted in the taken image as a person who is allowed to enter the imaging room R1.

For example, the storage circuit 132 is assumed to store technician authentication information associating a face photograph of each technician working at the medical institution in which the imaging room R1 is disposed with the identification information of each technician. The authentication function 133*j* specifies a face photograph matching a face of the technician 1 depicted in the taken image acquired from the camera 540 among face photographs of the technicians stored in the storage circuit 132, and specifies the identification information associated with the specified face photograph as the identification information of the technician 1 depicted in the taken image. In a case in which the identification information of the specified technician 1 matches the identification information of the technician 1 registered in the tablet terminal 200, the authentication function 133*j* authenticates the technician 1 as a person who is allowed to enter the imaging room R1.

The storage circuit 132 is also assumed to store the patient authentication information associating a face photograph of the patient P as an imaging target of the magnetic resonance imaging apparatus 100 with the identification information of the patient P. In a case in which the face photograph of the patient P stored in the storage circuit 132 matches a face of the patient P depicted in the taken image acquired from the camera 540, the authentication function 133j specifies the identification information of the patient P stored in the storage circuit 132 as the identification information of the patient P depicted in the taken image. In a case in which the identification information of the specified patient P matches the identification information of the patient P registered in the tablet terminal 200, the authentication function 133j authenticates the patient P as a person who is allowed to enter the imaging room R1.

The technician authentication information and the patient authentication information may be stored in a place outside the magnetic resonance imaging apparatus 100. A storage place may be, for example, a server apparatus in the medical institution, the tablet terminal 200, or the like.

The authentication method is not limited to the method described above. For example, the authentication function 133j may compare the identification information of the technician 1 or the patient P registered in an examination order of the magnetic resonance imaging apparatus 100, instead of the identification information of the technician 1 or the patient P registered in the tablet terminal 200, with the identification information of the technician 1 or the patient P specified from the taken image acquired from the camera 540. The authentication function 133j may acquire information of the examination order from an RIS and the like, or from the storage circuit 132 of the magnetic resonance imaging apparatus 100, for example.

The authentication function 133j sends out, to the electric lock control function 133d, whether the technician 1 or the patient P has been authenticated as a person who is allowed to enter the imaging room R1.

In a case in which it is detected that the tablet terminal 200 is placed on the tablet holder 510, and the authentication function 133j authenticates at least one of the technician 1 and the patient P, the electric lock control function 133d according to the present embodiment unlocks the door 500 of the entrance.

As described above, the magnetic resonance imaging apparatus 100 according to the present embodiment unlocks the door 500 of the entrance in a case in which it is detected that the tablet terminal 200 is placed on the tablet holder 510, and at least one of the technician 1 and the patient P who are present outside the imaging room R1 is authenticated. Thus, with the magnetic resonance imaging apparatus 100 according to the present embodiment, in addition to the effect of the first embodiment, the door 500 can be opened only in a case in which the technician 1 or the patient P who is allowed to enter the imaging room R1 is present in front of the door 500.

For example, in a case in which the identification information associated with the face of the patient P who is present in front of the door 500 of the imaging room R1 does not match the identification information of the patient registered as an inquiry target or the identification information of the patient registered in the examination order of the magnetic resonance imaging apparatus 100, the door 500 is not unlocked, so that occurrence of a patient mix-up can be reduced.

For example, in a case in which the identification information associated with the face of the technician 1 who is present in front of the door 500 of the imaging room R1 does not match the identification information of the technician registered as a user of the tablet terminal 200 or identification information of a technician in charge who is registered in association with the examination order of the magnetic resonance imaging apparatus 100, the door 500 is not unlocked, so that it is possible to reduce a case in which a person other than the technician 1 who can operate the magnetic resonance imaging apparatus 100 enters the imaging room R1 alone.

In the present embodiment, at least one of the technician 1 and the patient P who are present outside the imaging room R1 is assumed to be an authentication target, but the authentication of the patient P may be made mandatory, for example. Alternatively, the authentication of at least one technician 1 may be made mandatory.

In the present embodiment, the description has been made on the assumption that the electric lock control function 133d unlocks the door 500 in a case in which it is detected that the tablet terminal 200 is placed on the tablet holder 510, but the configuration according to the present embodiment may be applied to the configuration described in the second embodiment.

For example, as in the second embodiment described above, in a case in which the magnetic resonance imaging apparatus 100 includes the opening/closing appliance control function 133h, the opening/closing appliance control function 133h outputs the information related to permission for entry into the imaging room R1 through the entrance in a case in which it is detected that the tablet terminal 200 is placed on the tablet holder 510, and at least one of the technician 1 and the patient P is authenticated by the authentication function 133j.

The present embodiment describes face authentication as an example, but the authentication function 133j can employ various authentication methods such as voice authentication, iris authentication, or fingerprint authentication. The technician 1 or the patient P may be authenticated by the tablet terminal 200, the electric lock 400, or the tablet holder 510 instead of the magnetic resonance imaging apparatus 100, or another authentication device may be provided.

Fifth Embodiment

In the fourth embodiment described above, a recognition result of the technician 1 or the patient P positioned in front of the door 500 of the imaging room R1 is used for determining whether the technician 1 or the patient P is allowed to enter the imaging room R1. However, in a fifth embodiment, a setting of the magnetic resonance imaging apparatus 100 is changed in accordance with the technician 1 or the patient P who has been recognized.

The configuration of the magnetic resonance imaging apparatus 100 according to the present embodiment is the same as the configuration in the fourth embodiment. Similarly to the fourth embodiment, the processing circuit 133 of the magnetic resonance imaging apparatus 100 according to the present embodiment has the imaging processing function 133a, the first detection function 133b, the second detection function 133c, the electric lock control function 133d, the display control function 133e, the acceptance function 133f, the transmission/reception function 133g, and the authentication function 133j. The magnetic resonance imaging apparatus 100 is an example of the apparatus according to the present embodiment. The electric lock control function 133d is an example of the entry management unit according to the present embodiment.

The first detection function 133b, the second detection function 133c, the electric lock control function 133d, the acceptance function 133*f*, and the transmission/reception function 133*g* according to the present embodiment each have the same function as that in the fourth embodiment.

The authentication function 133*j* according to the present embodiment has the same function as that in the fourth embodiment. In the present embodiment, the authentication function 133*j* authenticates at least one patient P and at least one technician 1.

In addition to the function described in the first embodiment, the imaging processing function 133*a* according to the present embodiment changes the setting of the magnetic resonance imaging apparatus 100 in accordance with the patient P authenticated by the authentication function 133*j*.

For example, the imaging processing function 133*a* acquires the height of the patient P from the patient information of the patient P stored in the tablet terminal 200 based on the identification information of the authenticated patient P. The imaging processing function 133*a* controls the couch control circuit 106 to adjust the height of the couch 105 corresponding to the acquired height of the patient P. The height of the couch 105 is an example of the setting of the magnetic resonance imaging apparatus 100, and a change target is not limited thereto.

The imaging processing function 133*a* may acquire the patient information of the patient P from the storage circuit 132, or another server apparatus installed in the medical institution.

In a case in which the tablet terminal 200 is placed on the tablet holder 510, the imaging processing function 133*a* may acquire the information registered in the inquiry about the patient P from the tablet terminal 200, and set a plan for taking a magnetic resonance image based on the acquired information. More specifically, the imaging processing function 133*a* generates sequence information for imaging the patient P in accordance with the information registered in the inquiry about the patient P.

Alternatively, the imaging processing function 133*a* may start to prepare for imaging simply triggered by the tablet terminal 200 placed on the tablet holder 510 without acquiring the information registered in the inquiry from the tablet terminal 200.

In addition to the function described in the first embodiment, the display control function 133*e* according to the present embodiment causes the display 135 to display guidance information corresponding to the technician 1 authenticated by the authentication function 133*j*. More specifically, the display control function 133*e* according to the present embodiment causes the display 135 to display guidance information that is different depending on skill of the technician 1. The display 135 is an example of a display unit according to the present embodiment.

For example, the storage circuit 132 according to the present embodiment or another server apparatus installed in the medical institution is assumed to store the identification information of each technician and information representing the skill of each technician in association with each other. The information representing the skill of each technician may be included in the technician authentication information described in the fourth embodiment. The display control function 133*e* acquires the information representing the skill of the technician 1 from the technician authentication information stored in the storage circuit 132 and the like based on the identification information of the authenticated technician 1. The information representing the skill of each technician may be years of experience, or a level of the skill such as "high" and "low", for example.

The guidance information is, for example, characters or images representing a procedure of fixing the patient P in a posture appropriate for imaging, a procedure of coil setting to attach the RF coil to the patient P, an operation procedure of the magnetic resonance imaging apparatus 100, or the like. The guidance information may further include voice.

For example, in a case in which the skill of the authenticated technician 1 is high, the display control function 133*e* causes the guidance information including simple content to be displayed. In a case in which the skill of the authenticated technician 1 is low, the display control function 133*e* causes the guidance information including detailed content to be displayed.

As described above, the magnetic resonance imaging apparatus 100 according to the present embodiment authenticates the patient P who is present outside the imaging room R1, and changes the setting of the magnetic resonance imaging apparatus 100 in accordance with the authenticated patient P. Due to this, with the magnetic resonance imaging apparatus 100 according to the present embodiment, the setting of the magnetic resonance imaging apparatus 100 can be quickly changed in accordance with the patient P who enters the room, and improve efficiency of preparation before imaging.

As described above, the magnetic resonance imaging apparatus 100 according to the present embodiment authenticates the technician 1 who is present outside the imaging room R1, and causes the display 135 to display the guidance information corresponding to the authenticated technician 1. Due to this, the magnetic resonance imaging apparatus 100 according to the present embodiment can effectively support work of the technician 1 by displaying the guidance information appropriate for the technician 1 who enters the imaging room R1.

In the present embodiment, both of the technician 1 and the patient P are assumed to be authenticated, but only the technician 1, or only the patient P may be authenticated. In the present embodiment, the display control function 133*e* is assumed to cause the display 135 to display the guidance information that is different depending on the skill of the technician 1, but may cause the display 135 to display the guidance information that is different depending on a characteristic of the technician 1 other than the skill.

In the present embodiment, the description has been made on the assumption that the electric lock control function 133*d* unlocks the door 500 in a case in which it is detected that the tablet terminal 200 is placed on the tablet holder 510, but the configuration according to the present embodiment may be applied to the configuration including the opening/closing appliance control function 133*h* described in the second embodiment. The configuration according to the other embodiment may be combined with the configuration according to the present embodiment.

Sixth Embodiment

In a sixth embodiment, the magnetic resonance imaging apparatus 100 further has a function of locking the tablet terminal 200 placed on the tablet holder 510 not to be removed.

Figure 9:
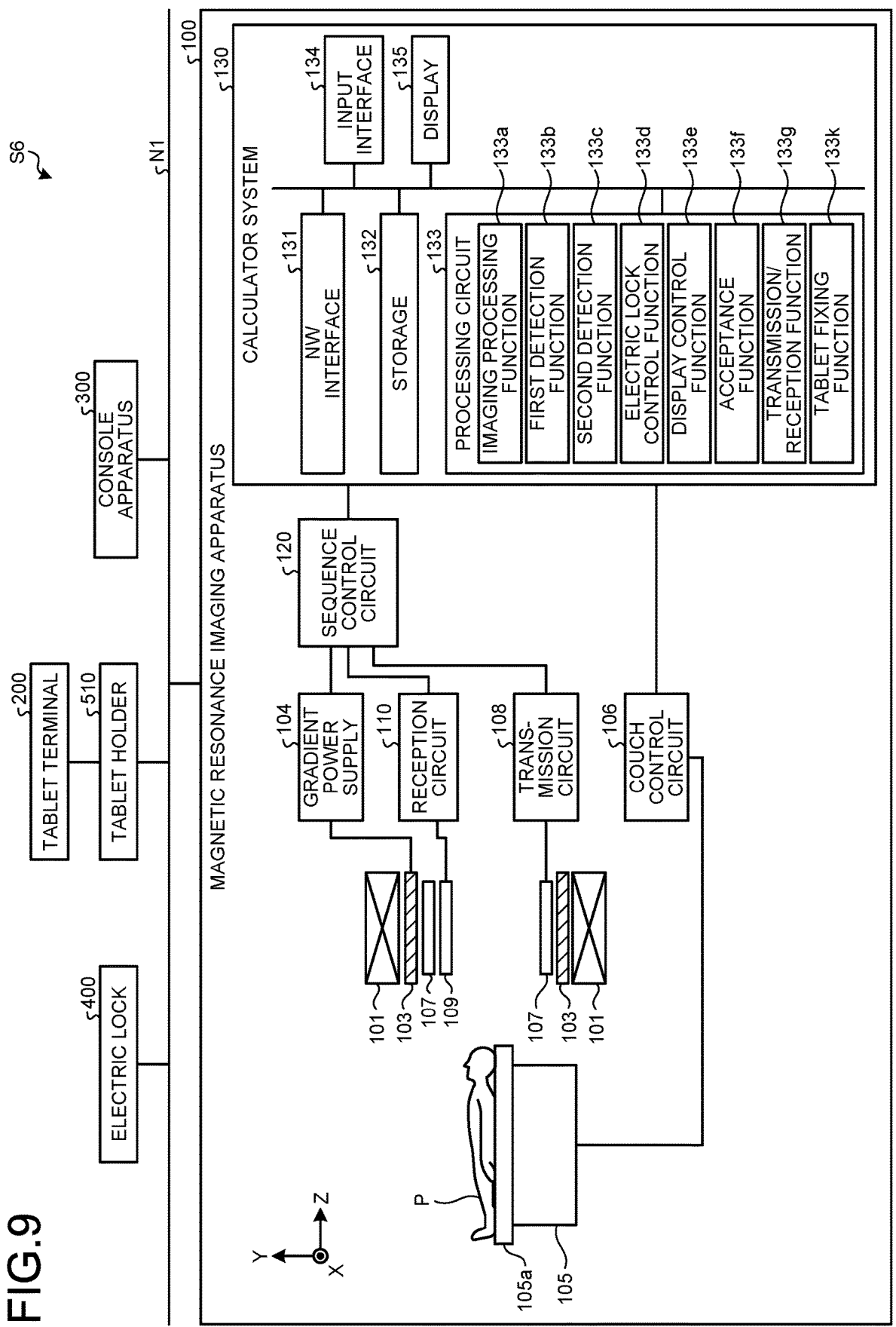
FIG. 9 is a block diagram illustrating an example of an entry management system including a magnetic resonance imaging apparatus according to a sixth embodiment.

FIG. 9 is a block diagram illustrating an example of an entry management system S6 including the magnetic resonance imaging apparatus 100 according to the sixth embodiment. The tablet holder 510 according to the present embodiment has a function of locking the tablet terminal 200 not to be removed.

The configuration of the magnetic resonance imaging apparatus 100 according to the present embodiment is the same as the configuration in the first embodiment. Similarly to the fourth embodiment, the processing circuit 133 of the magnetic resonance imaging apparatus 100 according to the present embodiment has the imaging processing function 133a, the first detection function 133b, the second detection function 133c, the electric lock control function 133d, the display control function 133e, the acceptance function 133f, the transmission/reception function 133g, and a tablet fixing function 133k. The tablet fixing function 133k is an example of a terminal fixing mechanism control unit and a terminal fixing mechanism controller. The magnetic resonance imaging apparatus 100 is an example of the apparatus according to the present embodiment. The electric lock control function 133d is an example of the entry management unit according to the present embodiment.

The imaging processing function 133a, the first detection function 133b, the second detection function 133c, the electric lock control function 133d, the display control function 133e, the acceptance function 133f, and the transmission/reception function 133g according to the present embodiment each have the same function as that in the first embodiment.

In a case in which the opening/closing state of the door 500 of the imaging room R1 detected by the second detection function 133c is the opened state, the tablet fixing function 133k controls the tablet holder 510 to fix the tablet terminal 200 to the tablet holder 510. In this state, the technician 1 cannot remove the tablet terminal 200 from the tablet holder 510.

When the technician 1 closes the door 500 of the imaging room R1, the tablet fixing function 133k controls the tablet holder 510 to enable the tablet terminal 200 to be removed from the tablet holder 510.

As described above, the magnetic resonance imaging apparatus 100 according to the present embodiment fixes the tablet terminal 200 to the tablet holder 510 in a case in which the opening/closing state of the door 500 of the imaging room R1 is the opened state. Due to this, the magnetic resonance imaging apparatus 100 according to the present embodiment can prevent the technician 1 from removing the tablet terminal 200 from the tablet holder 510 while the door 500 is opened. For example, when the technician 1 unlocks the door 500, and removes the tablet terminal 200 from the tablet holder 510 while the door 500 is opened, there is the possibility that the technician 1 accidentally enters the imaging room R1 while carrying the tablet terminal 200. In addition to the effect of the first embodiment, the magnetic resonance imaging apparatus 100 according to the present embodiment can reduce a case in which the technician 1 accidentally carries the tablet terminal 200 into the imaging room R1 after unlocking the door 500 as described above.

In the present embodiment, the magnetic resonance imaging apparatus 100 is assumed to have the same configuration as that in the first embodiment, but may be combined with the other embodiment. For example, the configuration according to the present embodiment may be applied to the configuration including the opening/closing appliance control function 133h described in the second embodiment.

First Modification

In the second embodiment described above, as a method of controlling entry into the imaging room R1 other than locking and unlocking of the door 500, exemplified is controlling movement of the bar 521 that is disposed outside the door 500 of the entrance of the imaging room R1. However, the method of controlling entry into the imaging room R1 is not limited thereto.

For example, in place of a mechanism that physically blocks passage of the technician 1 or the patient P such as the bar 521, a notification device may be disposed, the notification device that displays information related to permission for entry into the imaging room R1 through the entrance, or outputs the information by voice. The notification device may be, for example, the speaker 530, an indicator representing whether entry is allowed, a display, or a pilot lamp. The notification device is disposed outside the entrance of the imaging room R1, for example, in the vicinity of the door 500. Any one of such apparatuses may be disposed, or a plurality of apparatuses may be combined to be disposed. Alternatively, the display 201 or the speaker of the tablet terminal 200 may function as the notification device.

For example, similarly to the third embodiment, the magnetic resonance imaging apparatus 100 according to the present modification has the notification control function 133i. In a case in which the door 500 is caused to be in the opened state when it is not detected that the tablet terminal 200 is placed on the tablet holder 510, the notification control function 133i according to the present modification transmits a control signal to the notification device such as the speaker 530 to notify that entry is not permitted. Content of the notification may be a warning against the technician 1 who is about to enter the room, for example, or notification that notifies surrounding people of unauthorized entry.

In a case in which it is detected that the tablet terminal 200 is placed on the tablet holder 510, the notification control function 133i according to the present modification transmits a control signal to the notification device such as the speaker 530 to notify that entry is permitted. For example, the notification control function 133i controls the indicator to change display to represent that entry is allowed. The notification control function 133i may control the speaker 530 to turn off the warning in a case in which it is detected that the tablet terminal 200 is placed on the tablet holder 510.

The notification control function 133i is an example of an entry management unit according to the present embodiment. Transmission of the control signal to the notification device is an example of output of the information related to permission for entry into the imaging room R1 through the entrance.

Second Modification

A condition for locking and unlocking of the door 500 may be different depending on whether the magnetic resonance imaging apparatus 100 is performing imaging processing.

For example, in a case in which the tablet terminal 200 is moved away from the tablet holder 510 when the magnetic resonance imaging apparatus 100 is imaging the patient P, the electric lock control function 133d may cause the door 500 to be in the unlocked state. When the magnetic resonance imaging apparatus 100 is performing imaging processing, the patient P as an imaging target is present in the imaging room R1. Due to this, by causing the door 500 to be in the unlocked state even in a case in which the tablet terminal 200 is moved away from the tablet holder 510, a health professional for supporting the patient P can smoothly enter the imaging room R1 from the outside even when a certain emergency situation occurs.

In a case in which the tablet terminal 200 is moved away from the tablet holder 510 when the magnetic resonance imaging apparatus 100 is imaging the patient P, the electric lock control function 133d may maintain the unlocked state of the door 500 until the door 500 is manually locked by the technician 1 even when the imaging processing performed by the magnetic resonance imaging apparatus 100 ends.

The method of manually locking the door 500 is not specifically limited, and the door 500 may be locked by operating the door 500, or a knob, a switch, and the like disposed in the vicinity of the door 500 by the technician 1, for example. The acceptance function 133f of the magnetic resonance imaging apparatus 100 may accept an operation of locking the door 500 by the technician 1. Alternatively, the console apparatus 300 may accept the operation of locking the door 500 by the technician 1.

In a case in which the tablet terminal 200 is moved away from the tablet holder 510 when the magnetic resonance imaging apparatus 100 is imaging the patient P, the electric lock control function 133d may cause the door 500 to be in the unlocked state, and lock the door 500 after a certain time has elapsed thereafter.

In a case in which the tablet terminal 200 has a position information transmitting function such as a Global Positioning System (GPS) transmitter, the electric lock control function 133d may lock the door 500 in a case in which the tablet terminal 200 is moved away from the imaging room R1 by a certain distance or more.

Irrespective of whether imaging processing is being performed, the electric lock control function 133d may unlock the door 500 in a case in which the patient P presses a patient call button disposed on the magnetic resonance imaging apparatus 100, or in a case in which a system error occurs in the magnetic resonance imaging apparatus 100.

In a case in which the magnetic resonance imaging apparatus 100 has the tablet fixing function 133k described above in the sixth embodiment, a condition for locking the tablet terminal 200 may be different depending on whether the magnetic resonance imaging apparatus 100 is performing imaging processing.

For example, in a period from when the door 500 is unlocked until imaging of the patient P by the magnetic resonance imaging apparatus 100 is completed, the tablet fixing function 133k of the magnetic resonance imaging apparatus 100 may lock the tablet terminal 200 not to be removed from the tablet holder 510.

Third Modification

In the sixth embodiment described above, to reduce a case in which the tablet terminal 200 is carried into the imaging room R1, there is a limitation such that the tablet terminal 200 is prevented from being removed from the tablet holder 510 while the door 500 is opened. However, another method may be employed.

For example, in a case in which the door 500 of the imaging room R1 is in the opened state, and it is detected that the tablet terminal 200 is removed from the tablet holder 510, the notification control function 133i may cause the notification device such as the speaker 530 to notify information for calling attention to carrying the tablet terminal 200 into the imaging room R1.

For example, information for calling attention is voice information, character information, or the like such as "The door of the imaging room is opened. Return the tablet terminal to the certain position, close the door of the imaging room after confirming that nobody is present in the imaging room, and use the tablet terminal", but the information is not limited thereto.

Fourth Modification

In the embodiments described above, the imaging room R1 is assumed to have one entrance, but the imaging room R1 may include a plurality of entrances. In this case, similarly to the door 500, a lock using the tablet terminal 200 as a key may be disposed on each of doors of all the entrances. In a case in which the tablet terminal 200 is placed on any one of the doors, all of the doors may be caused to be in the unlocked state. Alternatively, a lock using the tablet terminal 200 as a key may be disposed only on the door 500 that is used for entry of the patient P, and the lock is not necessarily disposed on the other entrances.

Fifth Modification

In addition to placement of the tablet terminal 200 on the tablet holder 510, other units for unlocking the door 500 of the imaging room R1 may be prepared. For example, an operation unit for forcibly unlocking the door 500 may be disposed on the door 500 or in the vicinity of the door 500. The console apparatus 300 may accept the operation of forcibly unlocking the door 500 by the technician 1.

Sixth Modification

In the embodiments described above, the magnetic resonance imaging apparatus 100 is assumed to be an example of the apparatus, but the apparatus is not limited thereto. For example, the tablet terminal 200 may be an example of the apparatus.

In this case, the tablet terminal 200 is assumed to have the function described above as the function of the magnetic resonance imaging apparatus 100 in the embodiments described above. For example, the tablet terminal 200 may have the first detection function 133b, the second detection function 133c, and the electric lock control function 133d. The function of the tablet terminal 200 may further have another function.

Alternatively, the electric lock 400, the console apparatus 300, a server apparatus installed in the medical institution, or the like may be an example of the apparatus. In this case, the electric lock 400, the console apparatus 300, a server apparatus installed in the medical institution, or the like is assumed to have the function described above as the function of the magnetic resonance imaging apparatus 100 in the aforementioned embodiments.

The function described above as the function of the magnetic resonance imaging apparatus 100 in the embodiments described above may be implemented by a plurality of apparatuses in a distributed manner.

Seventh Modification

In the embodiments described above, locking and unlocking of the door 500 of the imaging room R1 are assumed to be performed by the magnetic resonance imaging apparatus 100 by controlling the electric lock 400 via wired or wireless communication, but locking and unlocking of the door 500 is not necessarily controlled via wireless or wired data communication. For example, in a case in which the tablet terminal 200 is placed on the tablet holder 510, the door 500 may be unlocked simply by an electrical contact signal or a mechanical switch. In a case of employing this configuration, the electric lock 400 or the mechanical switch disposed on the door 500 is an example of the entry management unit. In this case, the electric lock 400 may be an example of the apparatus.

Eighth Modification

In the embodiments described above, the electric lock 400 is assumed to be disposed on the door 500 of the imaging room R1, but a mechanical lock having a non-electric mechanical structure may be disposed thereon in place of the electric lock 400.

In the embodiments described above, an electrical detection method is exemplified as the method of "detecting that the tablet terminal 200 is placed on the tablet holder 510", but the detection method is not limited thereto. For example, the fact that the tablet terminal 200 is placed on the tablet holder 510 to press a mechanical switch may be simply assumed to be an example of detection. For example, both of the first detection unit and the entry management unit may be implemented by a mechanical configuration.

According to at least one of the embodiments described above, it is possible to reduce a case in which a health professional accidentally carries the tablet terminal into the imaging room in which the magnetic resonance imaging apparatus is installed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus, comprising:
   processing circuitry configured to:
      detect whether a mobile terminal is placed on a mobile terminal holder configured to hold the mobile terminal, the mobile terminal holder being located outside an entrance of a room in which a magnetic resonance imaging apparatus is installed, and
      execute unlocking of a door of the entrance, or outputting of information related to permission for entry into the room through the entrance, in response to detecting that the mobile terminal is placed on the mobile terminal holder.

2. The apparatus according to claim 1, wherein the processing circuitry is further configured to:
   notify precautions related to a high magnetic field generated from the magnetic resonance imaging apparatus before unlocking the door of the entrance or outputting the information related to permission for entry into the room through the entrance, in response to detecting that the mobile terminal is placed on the mobile terminal holder.

3. The apparatus according to claim 1, wherein the processing circuitry is further configured to;
   detect that the mobile terminal is placed by acquiring a signal indicating placement of the mobile terminal when the mobile terminal is placed on the mobile terminal holder, and
   unlock the door of the entrance in response to detecting that the mobile terminal is placed on the mobile terminal holder.

4. The apparatus according to claim 1, wherein the processing circuitry is further configured to:
   cause a notification device to notify precautions related to a high magnetic field generated from the magnetic resonance imaging apparatus before unlocking the door or outputting the information related to permission for entry into the room through the entrance, in response to detecting that the mobile terminal is placed on the mobile terminal holder.

5. The apparatus according to claim 4, wherein the processing circuitry is further configured to:
   detect an opening/closing state of the door, and
   cause the notification device to notify information for calling attention to carrying the mobile terminal into the room when the door of the room is in an opened state, and it is detected that the mobile terminal is removed from the mobile terminal holder.

6. The apparatus according to claim 1, wherein the processing circuitry is further configured to:
   detect an opening/closing state of the door, and
   fix the mobile terminal to the holder by controlling the holder when the door of the room is in an opened state.

7. The apparatus according to claim 1, wherein the processing circuitry is further configured to cause the door to be in an unlocked state in a period in which the mobile terminal is placed on the mobile terminal holder.

8. The apparatus according to claim 1, wherein the processing circuitry is further configured to cause the door to be in an unlocked state when the mobile terminal is moved away from the mobile terminal holder when the magnetic resonance imaging apparatus is performing imaging.

9. The apparatus according to claim 1, wherein
   the entrance also serves as an exit of the room, and
   the processing circuitry is further configured to enable the door to be opened from the inside of the room irrespective of whether the mobile terminal is placed at the mobile terminal holder.

10. The apparatus according to claim 1, wherein the processing circuitry is further configured to:
    authenticate at least one of a health professional and a patient who are present outside the room when it is detected that the mobile terminal is placed at the mobile terminal holder, and
    execute the unlocking of the door of the entrance, or output the information related to the permission for entry into the room through the entrance, when detecting that the mobile terminal is placed at the mobile terminal holder and having authenticated the at least one of the health professional and the patient.

11. The apparatus according to claim 10, wherein
    the apparatus is the magnetic resonance imaging apparatus, and
    the processing circuitry is further configured to;
       authenticate the patient who is present outside the room, and
       change a setting of the magnetic resonance imaging apparatus in accordance with the authenticated patient.

12. The apparatus according to claim 10, further comprising a display,
    wherein the processing circuitry is further configured to authenticate at least one health professional who is present outside the room, and cause the display to display guidance information corresponding to the authenticated health professional.

13. The apparatus according to claim 1, wherein the apparatus is the mobile terminal.

14. The apparatus according to claim 1, wherein the apparatus is an electric lock.

15. The apparatus according to claim 1, wherein the apparatus is a server apparatus configured to be connected to the magnetic resonance imaging apparatus.

16. A system comprising:
a mechanical switch configured to detect whether a mobile terminal is placed on a mobile terminal holder configured to hold the mobile terminal, the mobile terminal holder being located outside an entrance of a room in which a magnetic resonance imaging apparatus is installed; and
an electric lock configured to execute unlocking of a door of the entrance, or output information related to permission for entry into the room through the entrance, in response to detecting that the mobile terminal is placed on the mobile terminal holder.

17. A method, comprising:
detecting whether a mobile terminal is placed on a mobile terminal holder configured to hold the mobile terminal, the mobile terminal holder being located outside an entrance of a room in which a magnetic resonance imaging apparatus is installed; and
executing unlocking of a door of the entrance, or outputting of information related to permission for entry into the room through the entrance, in response to detecting that the mobile terminal is placed on the mobile terminal holder.

* * * * *